(12) United States Patent
Uesugi et al.

(10) Patent No.: US 10,017,730 B2
(45) Date of Patent: Jul. 10, 2018

(54) COMPOSTING ACCELERATORS FOR ORGANIC WASTE OR LIVESTOCK BEDDING

(71) Applicant: ASAHI CALPIS WELLNESS CO., LTD., Shibuya-ku, Tokyo (JP)

(72) Inventors: Taisuke Uesugi, Kanagawa (JP); Gentaro Yasuda, Kanagawa (JP)

(73) Assignee: Asahi Calpis Wellness Co., Ltd., Tokyo (JP)

(*) Notice: Subject to any disclaimer, the term of this patent is extended or adjusted under 35 U.S.C. 154(b) by 0 days.

(21) Appl. No.: 15/239,028

(22) Filed: Aug. 17, 2016

(65) Prior Publication Data

US 2016/0376545 A1 Dec. 29, 2016

Related U.S. Application Data

(62) Division of application No. 14/486,318, filed on Sep. 15, 2014, now Pat. No. 9,445,604.

(60) Provisional application No. 61/878,499, filed on Sep. 16, 2013.

(51) Int. Cl.
| | | |
|---|---|---|
| *A01N 63/02* | (2006.01) | |
| *C12N 1/20* | (2006.01) | |
| *A01N 63/00* | (2006.01) | |

(52) U.S. Cl.
CPC .............. *C12N 1/20* (2013.01); *A01N 63/00* (2013.01); *A01N 63/02* (2013.01); *Y02W 30/43* (2015.05)

(58) Field of Classification Search
None
See application file for complete search history.

(56) References Cited

U.S. PATENT DOCUMENTS

| | | | |
|---|---|---|---|
| 6,811,786 B1 | 11/2004 | Farmer | |
| 9,445,604 B2 * | 9/2016 | Uesugi | .................. A01N 63/02 |
| 2006/0188978 A1 | 8/2006 | Grant | |
| 2016/0286833 A1 * | 10/2016 | Yasuda | .................. A23K 10/18 |

FOREIGN PATENT DOCUMENTS

| | | | |
|---|---|---|---|
| CN | 103305446 | * | 9/2013 |
| EP | 1598122 A1 | | 11/2005 |
| JP | 2003-094095 A | | 4/2003 |
| JP | 2004-051380 A | | 2/2004 |
| JP | 2004-082110 A | | 3/2004 |
| JP | 2005-073639 A | | 3/2005 |
| JP | 2006-238820 A | | 9/2006 |
| JP | 4503530 B2 | | 7/2010 |
| JP | 2013-060378 A | | 4/2013 |
| JP | 2013-177271 A | | 9/2013 |
| RU | 2317670 C1 | | 2/2008 |
| RU | 2479975 C1 | | 4/2013 |

OTHER PUBLICATIONS

International Search Report dated Dec. 16, 2014, in PCT/JP2014/074067.

Swain et al., "Biocontrol and Other Beneficial Activities of *Bacillus subtilis* isolated from Cowdung Microflora," Microbiological Research, 2009, 164(2):121-130.

* cited by examiner

*Primary Examiner* — Ralph J Gitomer
(74) *Attorney, Agent, or Firm* — Foley & Lardner LLP

(57) ABSTRACT

This invention relates to a sterilization agent for livestock bedding or a composting accelerator for organic waste or livestock bedding, comprising at least one *Bacillus coagulans* thermophilic bacterium or a combination of the at least one *Bacillus coagulans* thermophilic bacterium and at least one *Bacillus subtilis* mesophilic bacterium, as an active ingredient, wherein the *Bacillus coagulans* thermophilic bacterium as a preferable bacterium is viable at a temperature of 40 to 60° C. and the *Bacillus subtilis* mesophilic bacterium is viable at a temperature of 30 to 50° C., and the mesophilic bacterium also has a sterilizing effect on harmful bacteria in bedding; and to a method for sterilizing livestock bedding or a method for accelerating composting of organic waste or livestock bedding by using these agents each as an active ingredient.

5 Claims, 2 Drawing Sheets ns for Solving the Problem

COMPOSTING ACCELERATORS FOR ORGANIC WASTE OR LIVESTOCK BEDDING

CROSS-REFERENCE TO RELATED APPLICATIONS

This application is a Divisional of U.S. application Ser. No. 14/486,318, filed Sep. 15, 2014, which claims priority from U.S. Provisional Application No. 61/878,499, filed Sep. 16, 2013.

FIELD OF THE INVENTION

The present invention relates to a method for sterilizing livestock bedding by using a predetermined *Bacillus coagulans* thermophilic bacterium or a combination of the *Bacillus coagulans* thermophilic bacterium and a *Bacillus subtilis* mesophilic bacterium. The sterilized bedding can be recycled as livestock bedding.

The present invention also relates to a method for accelerating composting of organic waste or bedding by using a predetermined *Bacillus coagulans* thermophilic bacterium or a combination of the *Bacillus coagulans* thermophilic bacterium and a *Bacillus subtilis* mesophilic bacterium.

BACKGROUND ART

It is known that *Bacillus* bacteria can be used for a treatment such as a treatment for composting organic waste.

For example, Patent Document 1 (JP Patent Publication (Kokai) No. 2013-060378A) describes an efficient method for sterilizing harmful bacteria, particularly odor-generating bacteria and pathogenic bacteria, in composting organic waste such as garbage or bedding or recycling bedding. This method employs at least one microorganism selected from the group consisting of *Bacillus*, *Geobacillus* and *Aeribacillus*.

Patent Document 2 (JP Patent No. 4503530) describes a method for treating organic waste, comprising allowing a mesophilic bacterium having activity at 15 to 50° C. and a thermophilic bacterium having activity at 50 to 70° C. to be present in organic waste. The mesophilic bacterium is *Bacillus subtilis* C-3102 strain (FERM BP-1096) and the thermophilic bacterium is *Bacillus pallidus* TK6004 strain (FERM BP-08597).

Patent Document 3 (JP Patent Publication (Kokai) No. 2006-238820A) discloses livestock bedding produced from livestock manure as a main raw material, by heating and sterilizing the raw material at high temperature while stirring, and then adding bacteria capable of decomposing and fermenting organic substances and useful bacteria capable of inhibiting pathogenic bacteria to the livestock, decomposing and fermenting organic components of livestock manure while stirring, simultaneously with amplifying useful bacteria inhibiting pathogenic bacteria to the livestock, and drying the livestock manure into grains. The publication also describes that sterilization is made by e.g., a burner at 90 to 110° C. for one to two or more hours.

PRIOR ART DOCUMENT

Patent Document

Patent Document 1: JP Patent Publication (Kokai) No. 2013-060378A
Patent Document 2: JP Patent No. 4503530
Patent Document 3: JP Patent Publication (Kokai) No. 2006-238820A

SUMMARY OF INVENTION

Problem to be Solved By the Invention

Livestock bedding once used is contaminated with livestock excrement (usually, excreta). In order to reuse the livestock bedding, it is necessary to kill harmful bacteria (contaminant), remove water to dry the bedding, and reduce level of ammonia. These treatments must be performed efficiently in a short period. A predetermined aerobic *Bacillus* bacterium developed by the present inventors is expected to be used for sterilization and composting of bedding. In a method using such a bacterium, fermentation heat is used to kill harmful bacteria and vaporize water. This method includes repeating an operation such as stacking formation of bedding, turning upside down (for oxygen supply) and spreading.

Sterilization using a microorganism is favorable in cost, since no heat source is required and has an advantage in that a large amount of bedding can be treated at a time. The key point of this approach is using a microorganism capable of killing harmful bacteria to a level where the harmful bacteria produce substantially no adverse effect. Whether the number of cells of a target harmful bacterium can be reduced to $\frac{1}{100,000}$ or less by fermentation heat is considered as a rough standard for such a microorganism. If such a useful microorganism can be found, bedding can be further effectively sterilized. However, since most of beddings used are persistent (hard-to-decompose) plant-derived beddings and wood-based beddings, growth of bacteria is more difficult than we thought and thus effective sterilization treatment cannot be achieved.

Means for Solving the Problem

The present inventors have now found that *Bacillus* bacteria or a combination of these bacteria capable of effectively sterilizing livestock bedding. Based on the finding, the present invention was accomplished herein.

The present invention includes the following features.

(1) A method for sterilizing livestock bedding, comprising a step of fermenting the bedding by adding at least one *Bacillus coagulans* thermophilic bacterium, or a combination of the at least one *Bacillus coagulans* thermophilic bacterium and at least one *Bacillus subtilis* mesophilic bacterium, to the livestock bedding.

(2) A method for accelerating composting of organic waste or livestock bedding, comprising a step of fermenting the organic waste or bedding by adding at least one *Bacillus coagulans* thermophilic bacterium, or a combination of the at least one *Bacillus coagulans* thermophilic bacterium and at least one *Bacillus subtilis* mesophilic bacterium, thereof to organic waste or livestock bedding.

(3) The method according to (1) or (2), in which the *Bacillus coagulans* thermophilic bacterium is viable at a temperature of at least 40 to 60° C.

(4) The method according to (1) or (2), in which the *Bacillus subtilis* mesophilic bacterium is viable at a temperature of at least 30 to 50° C.

(5) The method according to any of (1) to (4), using only fermentation heat of a microorganism.

(6) The method according to any of (1) to (3) and (5), in which the *Bacillus coagulans* thermophilic bacterium is selected from the group consisting of *Bacillus coagulans*

CP3424 strain (International Deposition Accession No. NITE BP-01692), *Bacillus coagulans* CP3425 strain (International Deposition Accession No. NITE BP-01693), and variants thereof.

(7) The method according to any of (1), (2), (4) and (5), in which the *Bacillus subtilis* mesophilic bacterium is *Bacillus subtilis* C-3102 strain (International Deposition Accession No. FERM BP-1096) or a variant thereof.

(8) The method according to any of (1) to (7), in which the *Bacillus coagulans* thermophilic bacterium is *Bacillus coagulans* CP3425 strain (International Deposition Accession No. NITE BP-01693) or a variant thereof, and the *Bacillus subtilis* mesophilic bacterium is *Bacillus subtilis* C-3102 strain (International Deposition Accession No. FERM BP-1096) or a variant thereof.

(9) *Bacillus coagulans* CP3424 strain (International Deposition Accession No. NITE BP-01692) or a variant thereof.

(10) *Bacillus coagulans* CP3425 strain (International Deposition Accession No. NITE BP-01693) or a variant thereof.

(11) A sterilization agent for livestock bedding, comprising at least one *Bacillus coagulans* thermophilic bacterium or a combination of the at least one *Bacillus coagulans* thermophilic bacterium and at least one *Bacillus subtilis* mesophilic bacterium, as an active ingredient.

(12) The sterilization agent according to (11), in which the *Bacillus coagulans* thermophilic bacterium is viable at a temperature of at least 40 to 60° C.

(13) The sterilization agent according to (11), in which the *Bacillus subtilis* mesophilic bacterium is viable at a temperature of at least 30 to 50° C.

(14) The sterilization agent according to (11) or (12), in which the *Bacillus coagulans* thermophilic bacterium is selected from the group consisting of *Bacillus coagulans* CP3424 strain (International Deposition Accession No. NITE BP-01692), *Bacillus coagulans* CP3425 strain (International Deposition Accession No. NITE BP-01693) and variants thereof.

(15) The sterilization agent according to (11) or (13), in which the *Bacillus subtilis* mesophilic bacterium is *Bacillus subtilis* C-3102 strain (International Deposition Accession No. FERM BP-1096) or a variant thereof.

(16) The sterilization agent according to any of (11) to (15), in which the *Bacillus coagulans* thermophilic bacterium is *Bacillus coagulans* CP3425 strain (International Deposition Accession No. NITE BP-01693) or a variant thereof, and the *Bacillus subtilis* mesophilic bacterium is *Bacillus subtilis* C-3102 strain (International Deposition Accession No. FERM BP-1096) or a variant thereof.

(17) A composting accelerator for organic waste or livestock bedding, comprising at least one *Bacillus coagulans* thermophilic bacterium, or a combination of the at least one *Bacillus coagulans* thermophilic bacterium and at least one *Bacillus subtilis* mesophilic bacterium, as an active ingredient.

(18) The composting accelerator for organic waste or livestock bedding according to (17), in which the *Bacillus coagulans* thermophilic bacterium is viable at a temperature of at least 40 to 60° C.

(19) The composting accelerator for organic waste or livestock bedding according to (17), in which the *Bacillus subtilis* mesophilic bacterium is viable at a temperature of at least 30 to 50° C.

(20) The composting accelerator according to (17) or (18), in which the *Bacillus coagulans* thermophilic bacterium is selected from the group consisting of *Bacillus coagulans* CP3424 strain (International Deposition Accession No. NITE BP-01692), *Bacillus coagulans* CP3425 strain (International Deposition Accession No. NITE BP-01693), and variants thereof.

(21) The composting accelerator according to (17) or (19), in which the *Bacillus subtilis* mesophilic bacterium is *Bacillus subtilis* C-3102 strain (International Deposition Accession No. FERM BP-1096) or a variant thereof.

(22) The composting accelerator according to any of (17) to (21), in which the *Bacillus coagulans* thermophilic bacterium is *Bacillus coagulans* CP3425 strain (International Deposition Accession No. NITE BP-01693) or a variant thereof, and the *Bacillus subtilis* mesophilic bacterium is *Bacillus subtilis* C-3102 strain (International Deposition Accession No. FERM BP-1096) or a variant thereof.

(23) A composition for accelerating sterilization or composting of bedding, containing a *Bacillus coagulans* thermophilic bacterium and a *Bacillus subtilis* mesophilic bacterium.

According to the present invention, the invention has an advantage in that livestock bedding can be effectively sterilized by use of a combination of predetermined *Bacillus* bacteria.

BRIEF DESCRIPTION OF THE DRAWINGS

FIG. 1 and FIG. 2 show just embodiments and the size of a stack is adjustable depending upon the individual cases.

MODE FOR CARRYING OUT THE INVENTION

Figure 1:
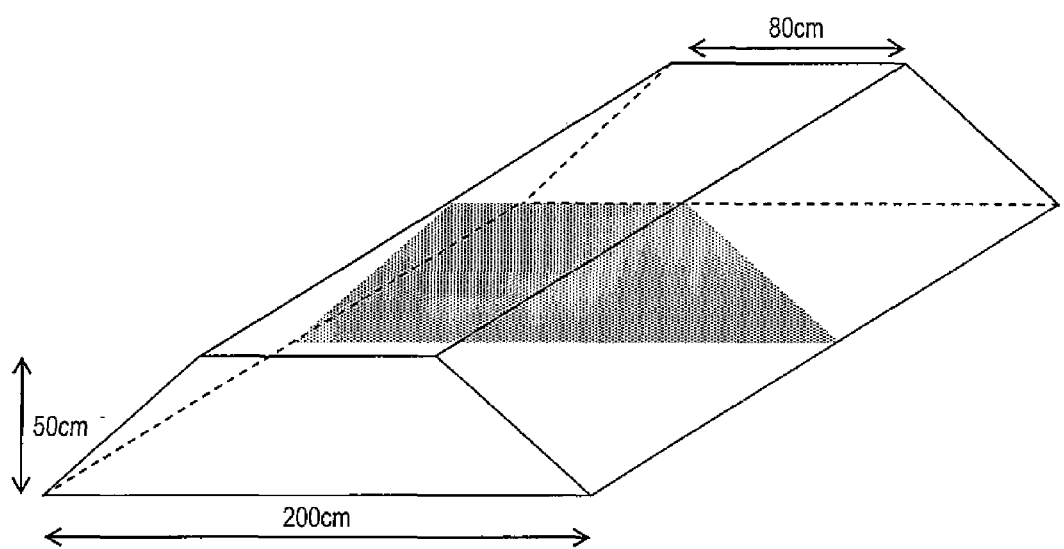
FIG. 1 shows a stack of bedding.

The present invention will be more specifically described.
1. Agent and Method for Sterilizing Livestock Bedding The present invention provides a method for sterilizing livestock bedding, comprising a step of fermenting the bedding by adding at least one *Bacillus coagulans* thermophilic bacterium, or a combination of the at least one *Bacillus coagulans* thermophilic bacterium and at least one *Bacillus subtilis* mesophilic bacterium, to the livestock bedding.

According to an embodiment of the present invention, the *Bacillus coagulans* thermophilic bacterium is viable at a temperature of at least 40 to 60° C. and has a sterilizing effect on harmful bacteria since the bacterium produces fermentation heat as the bacterium cells grow in the bedding.

According to another embodiment of the present invention, the *Bacillus subtilis* mesophilic bacterium is viable at a temperature of at least 30 to 50° C. and has a sterilizing effect on harmful bacteria since the bacterium produces fermentation heat as the bacterium cells grow in the bedding.

According to another embodiment of the present invention, in the above step, only fermentation heat of the microorganisms is characteristically used.

In this method, harmful bacteria to livestock, such as *Escherichia coli, Salmonella* bacteria and *Campylobacter* bacteria, which are contaminants in bedding, can be killed. According to experiments carried out by the present inventors, a temperature of 54° C. or more is required to effectively reduce or kill harmful bacteria in bedding, and the temperature is preferably maintained at 60° C. or more to obtain sterilization effect.

A *Bacillus coagulans* thermophilic bacterium has a nature of being viable at a temperature of 40 to 60° C. Other than this nature, the *Bacillus coagulans* thermophilic bacterium has an ability of increasing the temperature of bedding containing livestock excrement (usually, excreta) to 54° C. or more due to fermentation heat. Because of this, harmful bacteria in bedding can be effectively killed. The *Bacillus coagulans* thermophilic bacterium and/or *Bacillus subtilis* mesophilic bacterium can be screened, for example, by a livestock ammonia tolerance test followed by a fermentation test of bedding.

Specific examples of the *Bacillus coagulans* thermophilic bacterium include *Bacillus coagulans* CP3424 strain (International Deposition Accession No. NITE BP-01692), *Bacillus coagulans* CP3425 strain (International Deposition Accession No. NITE BP-01693), and variants thereof.

Specific examples of the *Bacillus subtilis* mesophilic bacterium include *Bacillus subtilis* C-3102 strain (International Deposition Accession No. FERM BP-1096) or a variant thereof.

A combination of preferable bacterial strains includes a combination of *Bacillus coagulans* CP3425 strain (International Deposition Accession No. NITE BP-01693) or a variant thereof as the *Bacillus coagulans* thermophilic bacterium and *Bacillus subtilis* C-3102 strain (International Deposition Accession No. FERM BP-1096) or a variant thereof as the *Bacillus subtilis* mesophilic bacterium.

*Bacillus coagulans* CP3424 strain (International Deposition Accession No. NITE BP-01692) and *Bacillus coagulans* CP3425 strain (International Deposition Accession No. NITE BP-01693) were deposited at the NITE Patent Microorganisms Depositary, National Institute of Technology and Evaluation (#122, 2-5-8 Kazusakamatari, Kisarazu-shi, Chiba 292-0818, Japan), which is an international authority depository, on Aug. 13, 2013, and the above international deposition accession numbers were assigned. These bacterial strains were identified to belong to *Bacillus coagulans* by comparing their 16S rDNA sequences to that of bacterial species known in the art.

According to the present invention, bedding can be sterilized by either one or both of these *Bacillus coagulans* thermophilic bacteria or by a combination of at least one of these *Bacillus coagulans* bacterial strains and a *Bacillus subtilis* mesophilic bacterium.

The *Bacillus subtilis* mesophilic bacterium is a bacterium capable of increasing the temperature of bedding to 40° C. or more due to fermentation heat when it is added to the bedding. Examples of a preferable mesophilic bacterium include *Bacillus subtilis* C-3102 strain (International Deposition Accession No. FERM BP-1096) or a variant thereof having substantially the same sterilizing effect as the C-3102 strain. The C-3102 strain was originally deposited on Dec. 25, 1985, at the International Patent Organisms Depositary of the National Institute of Advanced Industrial Science and Technology (at the time of deposition; the Fermentation Research Institute, Agency of Industrial Science and Technology of the Ministry of International Trade and Industry) located at 1-1-1 Higashi, Tsukuba, Ibaraki, Japan (at the time of deposition; 1-1-3, Higashi, Yatabe-cho, Tsukuba-gun, Ibaraki, Japan) under deposition No. FERM 8584; and transferred by the same institution to international deposition on Jun. 28, 1986 under deposition No. FERM BP-1096 (at the time of transfer; FERM 1096). The bacterial strain deposited is at present stored and controlled in the NITE Patent Microorganisms Depositary, National Institute of Technology and Evaluation (2-5-8 Kazusakamatari, Kisarazu-shi, Chiba, Japan, 292-0818). *Bacillus subtilis* C-3102 strain has been also deposited at a foundation of Taiwan, the Food Industry Research and Development Institute, Deposit of Biological Material for Patent Application, on November 14, 101 under the name of *Bacillus subtilis* C3102 (under deposition No. BCRC910568). The bacterial strain is described also in e.g., JP Patent Publications (Kokai) Nos. 63-209580A (1988) and 62-232343A(1987).

In the present invention, variants of the above three bacterial strains deposited may be used as long as they have the same sterilizing effects as those of respective parent strains. A variant can be obtained, for example, by culturing a parent strain in the presence of a chemical mutagen such as nitrosoguanidine, nitrosourea, methyl ethanesulfonate and derivatives thereof or by irradiating a parent strain with high energy beams such as UV ray, a gamma ray or X-ray.

The above three types of bacterial strains deposited or variants thereof to be used in the present invention may be added in the form of spores. The spore is a structure for protecting a bacterium itself, formed in an inhospitable environment, and can be germinated into a trophozoite when the conditions become favorable.

If the above bacterial strains, more specifically, a combination of CP3424 strain+C-3102 strain or a combination of CP3425 strain+C-3102 strain, is added to bedding, a higher sterilization effect is exerted than that of the addition of C-3102 strain alone (see Examples described later).

As described above, according to the present invention, sterilization of bedding can be effectively performed by combining a *Bacillus subtilis* mesophilic bacterium with at least one *Bacillus coagulans* thermophilic bacterium selected from the group consisting of *Bacillus coagulans* CP3424 strain (International Deposition Accession No. NITE BP-01692), *Bacillus coagulans* CP3425 strain (International Deposition Accession No. NITE BP-01693), and variants thereof.

When the *Bacillus coagulans* thermophilic bacterium or a combination of a *Bacillus coagulans* thermophilic bacterium and a *Bacillus subtilis* mesophilic bacterium is added to livestock bedding, each bacterium can be added, for example, in an appropriate amount to bedding; however, the amount of bacterium is not limited within such an appropriate range as long as the bacterium can grow in bedding and produce fermentation heat required for sterilization, in bedding.

Each of the bacterial strains can be aerobically cultured and amplified under culture conditions (culture medium, culture temperature and culture time) routinely used for culturing *Bacillus coagulans* or *Bacillus subtilis*.

The medium is a liquid medium or solid medium containing e.g., a carbon source, a nitrogen source and trace elements. More specifically, the medium may contain organic nitrogen sources such as peptone, polypeptone, meat extract, yeast extract, malt extract and corn steep liquor; inorganic nitrogen sources including ammonium salts such as ammonium sulfate and ammonium chloride and nitrates such as sodium nitrate; carbon sources such as glucose, sucrose, maltose, starch, sorbitol, maltooligosaccharide and dextrin; and inorganic salts such as phosphates, hydrochlorides, nitrates and sulfates of magnesium, calcium, sodium, potassium, iron, zinc and copper.

The culture temperature can be set within the range of 30 to 60° C. and the pH of the medium can be set within the range of 6.0 to 8.5.

The culture time can be set within the range of 10 to 72 hours. A bacterial strain after culture may be stored as a concentrate obtained by concentration by a separation method such as centrifugal separation or membrane separation, or as a dried product, which is obtained by drying the cultured strain using a drying method such as lyophilization.

According to the method for sterilizing bedding, a bacterial strain as mentioned above is added to bedding and fermentation is initiated and the resultant fermentation heat (fermentation temperature about 55 to 80° C.) is used for sterilization of the bedding. The time for sterilization treatment is not particularly limited; however, the time is usually 1 to 2 weeks.

Individual bacteria may be added simultaneously or separately. In the case of separate addition, preferably, a *Bacillus subtilis* mesophilic bacterium is added first. After temperature increase due to fermentation of bedding is confirmed, it is desirable to add a *Bacillus coagulans* thermophilic bacterium to the bedding.

Addition manner of bacteria is not particularly limited as long as they can uniformly add to the bedding. For example, addition can be made in such a manner that a bacterial suspension is prepared when used and is sprayed over bedding, or that bacterial cell powder is sprayed over bedding.

The livestock bedding refers to bedding for livestock such as a cock, a cow, a pig, a goat, a turkey and a quail. The "bedding" as used herein refers to litter tray or bedding for livestock, and generally formed of straw, chaff, grass or woody pieces (sawdust, etc.). As used herein, unless otherwise specified, the term "bedding" refers to a used one containing excrement (usually, excreta) of livestock and harmful bacteria. Examples of the harmful bacteria include *Escherichia coli*, *Salmonella* bacteria and *Campylobacter* bacteria, as mentioned above. Such harmful bacteria are killed and bedding can be recycled by the method of the present invention. Preferable bedding is poultry manure bedding or cow manure bedding.

The present invention further provides *Bacillus coagulans* CP3424 strain (International Deposition Accession No. NITE BP-01692) or a variant thereof, and *Bacillus coagulans* CP3425 strain (International Deposition Accession No. NITE BP-01693) or a variant thereof.

These bacterial strains or variants are as explained in the above. The variants have substantially the same sterilizing effect on harmful bacteria in bedding as those of respective parent strains. As used herein, the term "substantially the same" means that the levels of sterilization effect and/or the types of harmful bacteria may not be completely the same but virtually the same.

The present invention further provides a sterilization agent, for livestock bedding that can be used in the above sterilization method, containing at least one *Bacillus coagulans* thermophilic bacterium or a combination of the at least one *Bacillus coagulans* thermophilic bacterium and at least one *Bacillus subtilis* mesophilic bacterium, as an active ingredient.

According to an embodiment of the present invention, the *Bacillus coagulans* thermophilic bacterium is viable at a temperature of at least 40 to 60° C. and has a sterilizing effect on harmful bacteria due to fermentation heat produced as the bacterium cells grow in bedding.

According to another embodiment of the present invention, the *Bacillus subtilis* mesophilic bacterium is viable at a temperature of at least 30 to 50° C. and has a sterilizing effect on harmful bacteria due to fermentation heat produced as the bacterium cells grow in bedding.

A *Bacillus coagulans* thermophilic bacterium and *Bacillus subtilis* mesophilic bacterium can be screened from livestock bedding in accordance with the above screening procedure.

A specific example of the sterilization agent of the present invention is a sterilization agent containing the *Bacillus coagulans* thermophilic bacterium, which is selected from the group consisting of *Bacillus coagulans* CP3424 strain (International Deposition Accession No. NITE BP-01692), *Bacillus coagulans* CP3425 strain (International Deposition Accession No. NITE BP-01693), and variants thereof.

Another example of the sterilization agent of the present invention is a sterilization agent containing at least one *Bacillus coagulans* thermophilic bacterium, which is a bacterial strain selected from the group consisting of *Bacillus coagulans* CP3424 strain (International Deposition Accession No. NITE BP-01692), *Bacillus coagulans* CP3425 strain (International Deposition Accession No. NITE BP-01693) and variants thereof and a *Bacillus subtilis* mesophilic bacterium, which is *Bacillus subtilis* C-3102 strain (International Deposition Accession No. FERM BP-1096) or a variant thereof, as an active ingredient.

Preferable examples of the sterilization agent include a sterilization agent containing a *Bacillus coagulans* thermophilic bacterium, which is *Bacillus coagulans* CP3425 strain (International Deposition Accession No. NITE BP-01693) or a variant thereof; and a *Bacillus subtilis* mesophilic bacterium, which is *Bacillus subtilis* C-3102 strain (International Deposition Accession No. FERM BP-1096) or a variant thereof, as an active ingredient.

The sterilization agent of the present invention may be provided in the form of a mixture of the above bacterial strains or in the form of a so-called kit in which individual bacterial strains are separately packaged. Bacterial strains may take any form such as powder, granules, suspension, concentrate, or carrier-immobilized product, and may be present in any state such as solid, liquid, semisolid or gel, as long as they can be amplified when used.

The sterilization agent of the present invention may be in the form of a composition, more specifically, a composition for sterilizing bedding comprising a *Bacillus coagulans* thermophilic bacterium as defined above and a *Bacillus subtilis* mesophilic bacterium as defined above.

2. A Composting Accelerator and Composting Acceleration Method for Organic Waste or Livestock Bedding The present invention further provides a method for accelerating composting of organic waste or bedding, comprising a step of fermenting organic waste or the bedding by adding at least one *Bacillus coagulans* thermophilic bacterium, or a combination of the at least one *Bacillus coagulans* thermophilic bacterium and at least one *Bacillus subtilis* mesophilic bacterium, to the organic waste or the livestock bedding.

According to an embodiment of the present invention, the *Bacillus coagulans* thermophilic bacterium is viable at a temperature of at least 40 to 60° C. and has an acceleration effect of composting organic waste or livestock bedding.

According to another embodiment of the present invention, the *Bacillus subtilis* mesophilic bacterium is viable at a temperature of at least 30 to 50° C. and has an acceleration effect of composting organic waste or livestock bedding.

According to another embodiment of the present invention, in the above step, only fermentation heat of a microorganism as mentioned above is characteristically used.

The *Bacillus coagulans* thermophilic bacterium and the *Bacillus subtilis* mesophilic bacterium can be screened, for example, from livestock bedding in accordance with the above screening procedure.

A specific example of the *Bacillus coagulans* thermophilic bacterium is selected from the group consisting of *Bacillus coagulans* CP3424 strain (International Deposition Accession No. NITE BP-01692), *Bacillus coagulans* CP3425 strain (International Deposition Accession No. NITE BP-01693), and variants thereof.

A specific example of the *Bacillus subtilis* mesophilic bacterium is *Bacillus subtilis* C-3102 strain (International Deposition Accession No. FERM BP-1096) or a variant thereof.

A preferable combination of bacteria is a combination of a *Bacillus coagulans* thermophilic bacterium, which is *Bacillus coagulans* CP3425 strain (International Deposition Accession No. NITE BP-01693) or a variant thereof, and a *Bacillus subtilis* mesophilic bacterium, which is *Bacillus subtilis* C-3102 strain (International Deposition Accession No. FERM BP-1096) or a variant thereof.

Individual bacterial strains, agents, bedding, etc. are as described in Section 1 above and should be referred to the description of Section 1 in this Section.

The aforementioned method for sterilizing bedding can be further used for composting bedding no longer required or to be discarded and organic waste such as garbage discarded from production sites, cooking sites and household sites. More specifically, the bedding or organic waste is fermented by adding a combination of the above bacterial strains to the bedding or organic waste and the resultant fermentation heat is used to accelerate composting the organic waste or bedding. Since the fermentation temperature reaches about 55 to 80° C., fermentation is accelerated; at the same time, water is vaporized and harmful bacteria are killed. At the time of composting, preferably, bedding and organic waste are sometimes or always stirred or mixed to take air therein. In this manner, effective fermentation and composting can be made.

The amount of bacterial strain to be added by the method is determined as the amount at which the bacterial strain is amplified and composting is accelerated. The time required for composting treatment is not particularly limited; however it is usually 2 to 3 months.

The composts obtained by the above method can be used in the field of agriculture such as cultivation of plants.

The present invention further provides a composting accelerator for organic waste or livestock bedding, which can be used in a method for accelerating composting as mentioned above, containing at least one *Bacillus coagulans* thermophilic bacterium or a combination of the at least one *Bacillus coagulans* thermophilic bacterium and at least one *Bacillus subtilis* mesophilic bacterium, as an active ingredient.

According to an embodiment of the present invention, the *Bacillus coagulans* thermophilic bacterium is viable at a temperature of at least 40 to 60° C. and has an acceleration effect of composting organic waste or livestock bedding.

According to another embodiment of the present invention, the *Bacillus subtilis* mesophilic bacterium is viable at a temperature of at least 30 to 50° C. and has an acceleration effect of composting organic waste or livestock bedding.

The form of the agent is the same as described in the above sterilization agent, and should be specifically referred to the description of Section 1 above.

The *Bacillus coagulans* thermophilic bacterium and *Bacillus subtilis* mesophilic bacterium can be screened from livestock bedding in accordance with the above screening procedure.

A specific example of the composting accelerator of the present invention is a composting accelerator containing a *Bacillus coagulans* thermophilic bacterium, which is a bacterial strain selected from the group consisting of *Bacillus coagulans* CP3424 strain (International Deposition Accession No. NITE BP-01692), *Bacillus coagulans* CP3425 strain (International Deposition Accession No. NITE BP-01693), and variants thereof.

Another example of the composting accelerator of the present invention is a composting accelerator containing at least one *Bacillus coagulans* thermophilic bacterium selected from the group consisting of *Bacillus coagulans* CP3424 strain (International Deposition Accession No. NITE BP-01692), *Bacillus coagulans* CP3425 strain (International Deposition Accession No. NITE BP-01693) and variants thereof, and a *Bacillus subtilis* mesophilic bacterium, which is *Bacillus subtilis* C-3102 strain (International Deposition Accession No. FERM BP-1096) or a variant thereof, as an active ingredient.

A preferable example of the composting accelerator is a composting accelerator containing a *Bacillus coagulans* thermophilic bacterium, which is *Bacillus coagulans* CP3425 strain (International Deposition Accession No. NITE BP-01693) or a variant thereof, and a *Bacillus subtilis* mesophilic bacterium, which is *Bacillus subtilis* C-3102 strain (International Deposition Accession No. FERM BP-1096) or a variant thereof, as an active ingredient.

The composting accelerator of the present invention may be in the form of a composition, more specifically, a composition for accelerating composting of bedding composed of a *Bacillus coagulans* thermophilic bacterium defined above and a *Bacillus subtilis* mesophilic bacterium defined above.

EXAMPLES

The present invention will be more specifically described with reference to the following Examples, which should not be construed as limiting the technical scope of the present invention.

Example 1

1. Separation and Identification of Microorganism

Beddings sampled in Japan were each suspended and diluted with sterilized water. The diluted solution was smeared onto a standard agar medium or a CYC agar medium (ATCC medium 2591) and cultured at 50° C. or 60° C. to form colonies. A colony was isolated, purified and identified based on homology of the 16S rRNA gene sequence.

2. Screening Based on Ammonia Resistance

The bacterial strain cultured, separated and identified was suspended and diluted with sterilized water, and added dropwise to TS medium containing an ammonium salt and a high ammonium salt medium. The bacterial microorganisms were cultured at 50° C. for about 12 hours. Microorganisms were selected based on the size of colony in the TS medium containing an ammonium salt and the high ammonium salt medium. A *Bacillus licheniformis* group and a *Bacillus coagulans* group were selected by this method of selecting a microorganism having resistance to ammonia.

3. Screening by Fermentation Temperature

To bedding (600 kg) used for raising chickens and containing *Bacillus subtilis* C-3102 strain (FERM BP-1096) in an amount of 1×10⁵ cfu/g, the *Bacillus licheniformis* group and *Bacillus coagulans* group separated were added and mixed. After 4 to 5 days, bedding was turned upside down and fermented for further 4 days. Whether heat capacity during fermentation is improved or not by addition of the *Bacillus licheniformis* group or the *Bacillus coagulans* group was checked. The heat capacity was obtained by measuring temperature at three sites (FIG. 2) of a stack of bedding (FIG. 1) and making a calculation in accordance with Formula 1 (Table 1).

$$\text{Heat capacity} = \int_{t1}^{t2} 10^{\frac{T(t)-T(r)}{z}} Dt \qquad \text{[Formula 1]}$$

where $z=5$, $T(r)=54$, and $T(t)$=measured temperature.

TABLE 1-1

Heat capacity (relative value to C-3102 strain alone as 100)

|  | C-3102 strain alone | C-3102 strain + B. licheniformis group |
|---|---|---|
| Up | 100 | 118 |
| Down | 100 | 89 |
| Lateral | 100 | 74 |

TABLE 1-2

Heat capacity (relative value to C-3102 strain alone as 100)

|  | C-3102 strain alone | C-3102 strain + B. coagulans group |
|---|---|---|
| Up | 100 | 115 |
| Down | 100 | 145 |
| Lateral | 100 | 508 |

Figure 2:
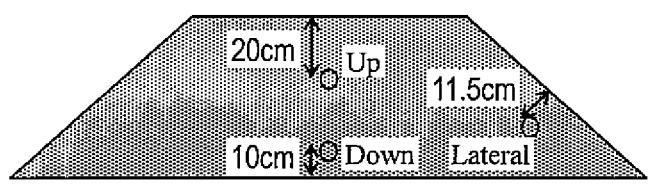
FIG. 2 shows a cross section of the stack of bedding, in which temperature measuring sites are shown. The sites measured are indicated as "Up" representing a site at a distance of 20 cm downward from the ceiling surface of the stack; "Down" representing a site at a distance of 10 cm upward from the bottom surface of the stack; and "Lateral" representing a site at a distance of 11.5 cm inward from the side surface.

In the Tables, the upper site (Up), lower site (Down) and lateral site (Lateral) represent the corresponding positions shown in FIG. 2.

As a result, it was found that heat capacity improves in the case where the *Bacillus coagulans* group was added, compared to the case where the *Bacillus licheniformis* group was added.

Next, whether each of bacterial strains constituting *Bacillus coagulans* group actually contributes to temperature increase of bedding was investigated. To bedding (500 kg) used for raising chickens and containing *Bacillus subtilis* C-3102 strain (FERM BP-1096) in an amount of 1×10⁵ cfu/g, *Bacillus coagulans* CP3424 strain and CP3425 strain, which are bacterial strains constituting the *Bacillus coagulans* group, were added and mixed. After 4 days, the bedding was turned upside down and fermented for further 4 days. Whether the heat capacity improves or not was checked. The heat capacity was obtained by measuring temperatures at three sites (FIG. 2) of a stack of bedding (FIG. 1) and making a calculation in accordance with Formula 1 (Table 2).

TABLE 2

Heat capacity (relative value to C-3102 strain alone as 100)

|  | C-3102 strain alone | C-3102 strain + CP3424 strain | C-3102 strain + CP3425 strain |
|---|---|---|---|
| Up | 100 | 308 | 990 |
| Down | 100 | 90 | 313 |
| Lateral | 100 | 134 | 303 |

As a result, it was found that the heat capacity increases in the cases where *Bacillus coagulans* CP3424 strain and *Bacillus coagulans* CP3425 strain were added compared to the case containing only *Bacillus subtilis* C-3102 strain (FERM BP-1096). Particularly, the heat capacity of *Bacillus coagulans* CP3425 strain at the "Up" site was about 10 times as large as that of *Bacillus subtilis* C-3102 strain. From these results, it can be said that the temperature increase of bedding can be accelerated by addition of *Bacillus coagulans* CP3424 strain and CP3425 strain, and that the bedding can be effectively sterilized by increasing heat capacity in this way.

Example 2

1. Confirmation of Temperature of Fermentation Using Defatted Soybean

Sporulated *Bacillus subtilis* C-3102 strain (FERM BP-1096) and sporulated *Bacillus coagulans* CP3425 strain were separately suspended in water and mixed with defatted soybean (500 g). Each of the mixtures was filled in a foamed polystyrene container and cultured. The temperature change at the center portion in the container was measured for 3 days. The heat capacity was obtained by measuring a temperature at the center portion in the foamed polystyrene container and was calculated by Formula 1 (Table 3).

TABLE 3

Heat capacity (relative value to C-3102 strain alone as 100)

|  | Relative heat capacity |
|---|---|
| C-3102 strain | 100 |
| CP3425 strain | 2585 |

INDUSTRIAL APPLICABILITY

As a result, the heat capacity of the case where *Bacillus coagulans* CP3425 strain was added was high compared to the case where *Bacillus subtilis* C-3102 strain (FERM BP-1096) was added.

The present invention made it possible to effectively sterilize livestock bedding and reuse the bedding. This is useful for livestock industry.

DEPOSIT

*Bacillus coagulans* CP3424 strain (International Deposition Accession No. NITE BP-01692).

*Bacillus coagulans* CP3425 strain (International Deposition Accession No. NITE BP-01693).

*Bacillus subtilis* C-3102 strain (International Deposition Accession No. FERM BP-1096).

The invention claimed is:

1. A composting accelerator for organic waste or livestock bedding, comprising at least one *Bacillus coagulans* thermophilic bacterium, or a combination of the at least one *Bacillus coagulans* thermophilic bacterium and at least one *Bacillus subtilis* mesophilic bacterium, as an active ingredient, wherein the *Bacillus coagulans* thermophilic bacterium is selected from the group consisting of *Bacillus coagulans* CP3424 strain (International Deposition Accession No. NITE BP-01692), *Bacillus coagulans* CP3425 strain (International Deposition Accession No. NITE BP-01693).

2. The composting accelerator for organic waste or livestock bedding according to claim 1, wherein the *Bacillus coagulans* thermophilic bacterium is viable at a temperature of at least 40 to 60° C.

3. The composting accelerator for organic waste or livestock bedding according to claim 1, wherein the *Bacillus subtilis* mesophilic bacterium is viable at a temperature of at least 30 to 50° C.

4. The composting accelerator according to claim 1, wherein the *Bacillus subtilis* mesophilic bacterium is *Bacillus subtilis* C-3102 strain (International Deposition Accession No. FERM BP-1096).

5. The composting accelerator according to claim 1, wherein the *Bacillus coagulans* thermophilic bacterium is *Bacillus coagulans* CP3425 strain (International Deposition Accession No. NITE BP-01693), and the *Bacillus subtilis* mesophilic bacterium is *Bacillus subtilis* C-3102 strain (International Deposition Accession No. FERM BP-1096).

* * * * *